US010767197B2

(12) United States Patent
Buyondo et al.

(10) Patent No.: US 10,767,197 B2
(45) Date of Patent: Sep. 8, 2020

(54) METHOD TO ENHANCE YEAST GROWTH FOR FERMENTATIVE BIOPRODUCT PRODUCTION, AND NUTRIENT COMPOSITION FOR SAME

(71) Applicant: Buckman Laboratories International, Inc., Memphis, TN (US)

(72) Inventors: John Paul Buyondo, Cordova, TN (US); Percy Jaquess, Memphis, TN (US)

(73) Assignee: BUCKMAN LABORATORIES INTERNATIONAL, INC., Memphis, TN (US)

( * ) Notice: Subject to any disclaimer, the term of this patent is extended or adjusted under 35 U.S.C. 154(b) by 204 days.

(21) Appl. No.: 15/297,717

(22) Filed: Oct. 19, 2016

(65) Prior Publication Data

US 2017/0107543 A1 Apr. 20, 2017

Related U.S. Application Data

(60) Provisional application No. 62/243,717, filed on Oct. 20, 2015.

(51) Int. Cl.
*C12P 7/06* (2006.01)
*C12N 1/16* (2006.01)
*C12N 1/38* (2006.01)
*C12N 1/18* (2006.01)
*C12P 7/64* (2006.01)

(52) U.S. Cl.
CPC .............. *C12P 7/06* (2013.01); *C12N 1/16* (2013.01); *C12N 1/18* (2013.01); *C12N 1/38* (2013.01); *C12P 7/6463* (2013.01); Y02E 50/17 (2013.01)

(58) Field of Classification Search
None
See application file for complete search history.

(56) References Cited

U.S. PATENT DOCUMENTS

| 2,817,624 | A | 12/1957 | Dulaney |
| 3,331,863 | A | 7/1967 | Campbell |
| 4,546,078 | A | 10/1985 | Manecke et al. |
| 5,843,734 | A | 12/1998 | Shonaka et al. |
| 6,448,298 | B1 | 9/2002 | Romualdo et al. |
| 7,955,826 | B2 | 6/2011 | Holt et al. |
| 2008/0226727 | A1* | 9/2008 | Kessell ............... A61K 8/06 424/489 |
| 2011/0230394 | A1 | 9/2011 | Wiatr et al. |
| 2012/0317877 | A1 | 12/2012 | Rangaswamy et al. |
| 2013/0084615 | A1 | 4/2013 | Van Groll |

FOREIGN PATENT DOCUMENTS

| EP | 0108231 A1 | 5/1984 |
| KR | 20030075996 A | 9/2003 |
| WO | WO 1992-2022369 A1 * | 12/1992 |
| WO | 2009113099 A2 | 9/2009 |

OTHER PUBLICATIONS

Futcher et al. A Sampling of the Yeast Proteome. Molecular and Cellular Biology (1999), 19(11): 7357-7368).*
Communication Relating to the Results of the Partial International Search issued in corresponding International Patent Application No. PCT/US2016/057688 dated Jan. 23, 2017 (10 pages).
Amartey et al., "Comparison of Corn Steep Liquor With Other Nutrients in the Fermentation of D-Xylose by Pichia Stipitis CBS 6054," Biotechnology Letters, 1994, vol. 16, No. 2, pp. 211-214.
Anschau et al., "A Cost Effective Fermentative Production of Glutathione by *Saccharomyces cerevisiae* with Cane Molasses and Glycerol," Brazilian Archives of Biology and Technology, 2013, vol. 56, No. 5, pp. 849-857.
Chin et al., "Bioprocess optimization for biomass production of probiotics yeast *Saccharomyces boulardii* in semi-industrial scale," Journal of Chemical and Pharmaceutical Research, 2015, vol. 7, No. 3, pp. 122-132.
Shah et al., "Ethanol Production Kinetics by a Thermo-Tolerant Mutant of *Saccharomyces cerevisiae* from Starch Industry Waste (Hydrol)," Pak. J. Anal. Environ. Chem., 2010, vol. 11, No. 1, pp. 16-21.
International Search Report and Written Opinion issued in corresponding International Patent Application No. PCT/US2016/057688 dated Mar. 17, 2017 (20 pages).
Yamada et al., "Direct ethanol production from cellulosic materials using a diploid strain of *Saccharomyces cerevisiae* with optimized cellulase expression," Biotechnology for Biofuels, 2011, vol. 4, No. 8, pp. 1-8.
Office Action issued in corresponding European Patent Application No. 16 791 175.9 dated Apr. 20, 2020 (6 pages).

* cited by examiner

Primary Examiner — Iqbal H Chowdhury
(74) Attorney, Agent, or Firm — Kilyk & Bowersoc, P.L.L.C.

(57) ABSTRACT

A method for enhancing yeast growth for bioproduct production is described. A method for fermentative bioproduct production also is provided. A nutrient composition used in the methods also is described. A liquid mixture containing the nutrient composition, yeast culture (or fungi, algae, or bacteria culture), and sugars also is provided.

28 Claims, 7 Drawing Sheets

METHOD TO ENHANCE YEAST GROWTH FOR FERMENTATIVE BIOPRODUCT PRODUCTION, AND NUTRIENT COMPOSITION FOR SAME

This application claims the benefit under 35 U.S.C. § 119(e) of prior U.S. Provisional Patent Application No. 62/243,717, filed Oct. 20, 2015, which is incorporated in its entirety by reference herein.

BACKGROUND OF THE INVENTION

The present invention relates to a method for enhancing yeast growth for cell culturing and fermentative bioproduct production, and a nutrient composition for such uses, and a fermentable biomass mixture that contains the nutrient composition.

Microorganisms are used in fermentations to produce many kinds of products, such as ethanol, acetone, butanol, organic acids, lipids, oils, enzymes, proteins, special carbohydrates, antibiotics, and other products. Ethanol production from fermentation of biomass has received significant attention in recent years as a source of alternative fuel or biofuel.

Various additives have been described for use in cell culturing and production processes for fermentations with an objective of improving these operations.

Amartey, S., et al., "*Comparison of corn steep liquor with other nutrients in the fermentation of D-xylose by Pichia stipitis CBS 6054.*" Biotechnology letters 16.2 (1994): 211-214, describes the use of media containing corn steep liquor as the only source of nitrogen, amino acids, vitamins and other nutrients in the fermentation of D-xylose by a xylose fermenting yeast, and comparatively evaluates the efficacy of the media containing corn steep liquor with other media containing other sources of nitrogen in promoting yeast growth.

U.S. Patent Application Publication No. 2012/0317877 A1 describes a method for biodiesel production by yeast fermentation which uses raw materials including crude glycerol and corn steep liquor.

U.S. Patent Application Publication No. 2013/0084615 A1 describes a method for producing ethanol and yeast protein feed with whey permeate and nutrient source, wherein the method has inoculating, seeding, propagating steps, and fermenting steps. The nutrient source in the inoculating, seeding, and propagating steps is described as containing liquid ammonium phosphate and corn steep liquor, and other components such as urea ammonium nitrate, antibiotics, and hydrogen peroxide.

U.S. Pat. No. 5,843,734 describes an antifoaming agent for a fermentation process, wherein the antifoaming agent is a reaction product that is obtained by adding a specified ratio amount of ethylene oxide and propylene oxide to a mixture of an oil or fat and a polyhydric alcohol, and at least one compound selected from fatty acids, alcohols, polyoxyalkylene polyhydric alcohol ethers, polyoxyalkylene alkyl ethers, polyoxyalkylene fatty acid esters, polyoxyalkylene alkyl ether fatty acid esters, and polyoxyalkylene polymers.

U.S. Pat. No. 6,448,298 B1 describes a defoamer for alcoholic fermentations, wherein the defoamer is an aqueous composition which comprises a polydimethylsiloxane oil, an ethylene oxide/propylene oxide block copolymer, and a silicone/silica blend, in a specified ratio.

U.S. Pat. No. 7,955,826 B2 describes a method and composition for the production of ethanol by a *Saccharomyces* spp. during fermentation of a feedstock substrate in the fermentation medium which comprises adding an emulsion comprising a monoterpene and a surfactant or combination of surfactants. Surfactants are described that include ethoxylated alcohols, ethoxylated carbohydrates, ethoxylated vegetable oils, polyethyleneglycols (PEG), polypropylene glycols (PPG), monoesters and diesters of PEG and PPG, ethoxylated amines, fatty acids, ethoxylated fatty acids, fatty amides, and fatty diethanolamides, and specific examples of commercial sources of the surfactants.

Previous nutrient based products used in fermentations do not necessarily significantly increase yeast cell number or increase yeast cell viability, budding, and vitality. Previous nutrient products, when used in yeast propagation and fermentation, also do not necessarily increase yeast cell high ethanol concentration tolerance or increase oil extraction. Improved nutrient based products for cell culturing, propagating, and fermentations are needed which can reliably provide for improved results in these and other respects.

SUMMARY OF THE PRESENT INVENTION

A feature of the present invention is to provide a method for enhancing yeast growth, propagation, viability, budding, or vitality, or any combinations of these in cell culturing and/or bioproduct production. A further feature of the present invention is to provide a nutrient composition which provides increased efficiency, productivity, or high ethanol concentration tolerance, or any combinations of these in fermentative bioproduct production. Another feature of the present invention is to provide a fermentable biomass mixture that contains such a nutrient composition.

Additional features and advantages of the present invention will be set forth in part in the description which follows, and in part will be apparent from the description, or may be learned by practice of the present invention. The objectives and other advantages of the present invention will be realized and obtained by means of the elements and combinations particularly pointed out in the written description and appended claims.

To achieve these and other advantages and in accordance with the purposes of the present invention, as embodied and broadly described herein, the present invention relates to a method for enhancing yeast growth for bioproduct production, comprising culturing at least one yeast in a growth medium containing a nutrient composition to obtain a propagated yeast culture, wherein the nutrient composition comprises corn steep liquor and at least one of (a) at least one antifoaming agent, or (b) at least one surfactant, or any combination thereof.

The present invention further relates to a method for fermentative bioproduct production, comprising culturing at least one yeast in a growth medium containing a nutrient composition to obtain a propagated yeast culture, wherein the nutrient composition comprises corn steep liquor and at least one of (a) at least one antifoaming agent, or (b) at least one surfactant, or any combination thereof; inoculating a fermentation substrate with the propagated yeast culture to produce a fermentable biomass; fermenting the fermentable biomass to produce a fermented biomass comprising at least one bioproduct and non-fermented solids content; and separating at least a portion of the at least one bioproduct from the solids content.

The present invention also relates to a fermentation nutrient composition comprising corn steep liquor; and at least one of (a) at least one surfactant that is a nonionic surfactant, an amphoteric surfactant, or any combination thereof, or (b) at least one antifoaming agent, or any combination thereof.

The present invention further relates to a liquid mixture comprising corn steep liquor; and at least one of (a) at least one surfactant, or (b) at least one antifoaming agent, or any combination thereof; yeast culture; and sugars.

It is to be understood that both the foregoing general description and the following detailed description are exemplary and explanatory only and are only intended to provide a further explanation of the present invention, as claimed. The accompanying drawings, which are incorporated in and constitute a part of this application, illustrate several features of the present invention and together with the written description, serve to explain the principles of the present invention.

DETAILED DESCRIPTION OF THE PRESENT INVENTION

The present invention relates to improvements in cell culturing and bioproduct production that are obtained using a nutrient composition that combines at least corn steep liquor and at least one other component that is at least one antifoaming agent, or at least one surfactant, or any combination thereof. As an option, the nutrient composition can combine corn steep liquor, at least one antifoaming agent, and at least one surfactant. It is found that the nutrient composition of the present invention can increase yeast health and/or productivity in yeast growth and/or bioproduct fermentation stages. A good healthy yeast culture from the propagator is useful for efficient conversion of substrates such as corn to ethanol at the fermentation stage. For good growth, yeast cells require good oxygen transfer rate and essential nutrients like nitrogen, amino acids, vitamins, and/or minerals. The nutrient composition of the present invention is formulated to provide one or more of these vital nutrients to yeast cells, and/or improve fermentation media oxygen transfer rate for higher yeast cell count, and/or higher yeast cell viability, and/or better yeast cell budding, and/or yeast cell vitality, or any combinations of these. Supplying yeast cells with required nutrients can lead to improved efficient conversion of sugars to ethanol and/or higher ethanol productivity.

As further shown in the experimental testing results described herein, nutrient compositions of the present invention can provide increased yeast cell growth concentrations, increased ethanol production, and/or high ethanol concentration tolerance, as compared to corn steep liquor alone. The nutrient compositions of the present invention can provide increased ethanol production with high gravity fermentation as compared to commonly used nutrients such as urea. The fermentative bioproduct production that can be improved with use of the nutrient composition of the present invention can relate to production of ethanol, oils, biodiesel, acetone, butanol, organic acids, enzymes, proteins, antibiotics, or other fermentation products. Fermentable biomass mixtures that contain the nutrient composition also are provided. Yeast is used for sake of illustration in some descriptions provided herein, but other host microorganisms may be used. The nutrient composition of the present invention can be used for enhancing growth in all types of desired host microorganisms, such as yeasts, fungi, algae, bacteria, or others.

Figure 1A:
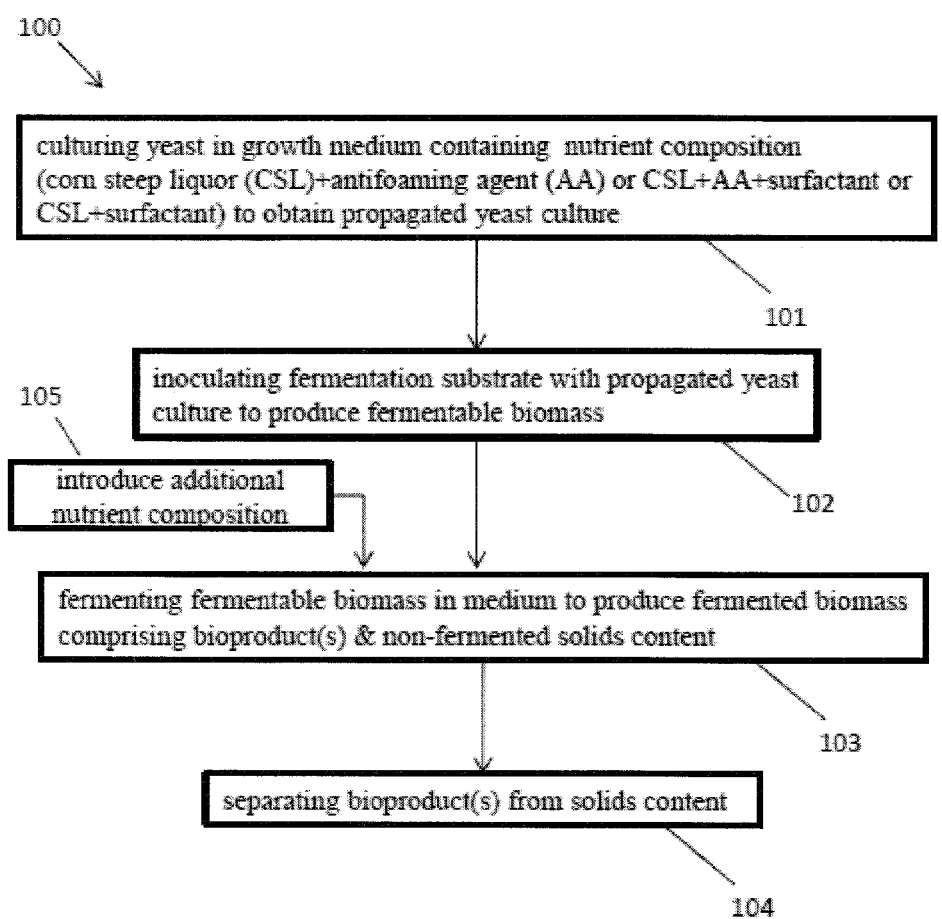
FIG. 1A illustrates a general process flow diagram for fermentative bioproduct production using a nutrient composition according to an example of the present invention.

In FIG. 1A, one example of a process flow for using a nutrient composition of the present invention in a fermentation operation is shown. The process flow, indicated by reference number 100, includes steps 101 (yeast culturing, including cell propagation), 102 (fermentation substrate inoculation), 103 (fermentation), and 104 (product recovery). As an option, additional nutrient composition can be added at the fermentation stage, as indicated by box 105. The culturing performed in the fermentation step (103) can be performed as a batch fermentation, fed-batch fermentation, or continuous fermentation. Additional steps may be included which are not shown in FIG. 1A, such as an initial yeast strain inoculating step and/or seeding step prior to step 101, the yeast culturing step 101 may comprise multiple stages, or combinations of these or other steps. The contents of the culture media can be heated in step 101, 103, or both, to maintain temperatures that support or promote cell growth or fermentation as applicable. The nutrient compositions of the present invention can be used in typical cell culturing and fermentation set-ups and operational conditions with adjustments or adaptions not necessarily needed other than may be for handling increased cell growth that can accompany use of the nutrient composition.

As used herein, "culturing" can refer to a process by which cells (e.g., yeast cells) are grown in a culture medium under controlled conditions. In some options, culturing refers to cell seeding, or cell propagating, or combinations of these. In some options, culturing includes fermenting. The term "seeding" can refer to the initiation of growth of yeast cultures. The term "propagating" can refer to exponential growth of yeast cultures on the growth medium. The term "fermenting" can refer to conversion of sugar to carbon dioxide and alcohol and/or other products by a microorganism, e.g., the conversion of glucose to ethanol by yeast. As used herein, "culture medium" (or "growth medium" or "fermentation medium") can refer to a liquid or gel designed to support the growth of microorganisms or cells, for example, yeast cells. A base culture medium can be used in any of seeding, propagating, and fermenting steps which can be provided in liquid form or broth. The base culture medium can contain a carbon source (e.g., sugar, starch) and water, and optionally other components, such as inorganic salts (e.g., $MgSO_4$, $K_2PO_4$). The nutrient composition of the present invention provides a nitrogen source, which can reduce or eliminate the need to include a nitrogen source in the base culture medium.

As indicated, the nutrient composition of the present invention can provide increased efficiency, productivity, or high ethanol concentration tolerance, or any combinations of these or other improvements in fermentative bioproduct production. Other improvements that may be provided with use of the nutrient composition of the present invention can include one or more of improved plant runability, the ability to run high gravity fermentations, reduced production cost, reduced usage of corn oil recovery chemistry, reduced solids, reduced distillers drying time, reduced energy (gas) consumption, shortened fermentation cycle time, reduced $NO_x$ production, or enhanced dewatering of fermentation mash, or other benefits.

In some options, the nutrient composition of the present invention is added to yeast propagation and fermentation tanks in ethanol or biodiesel production to achieve higher yeast cell growth, increased ethanol production, and increased oil recovery and/or extraction. The term "oil" as used herein, with respect to oil isolated from or produced by yeast, refers to lipids produced in yeast, and/or lipids and/or total lipid content isolated from yeast. The lipids can contain primarily triglycerides, but can also contain fatty acids, diglycerides and/or monoglycerides. As used herein, the term "fat" is understood to include "lipids". Corn oil, for example, refers to oil derived from that plant, such as a byproduct of bioethanol production. As used herein, "biodiesel" refers to diesel fuel comprising long-chain alkyl (methyl, propyl or ethyl) esters, such as fatty acid methyl esters of oil isolated from yeast, including chemical variants or modifications thereof. A raw or isolated sugar product or starch product, starchy crop, cellulosic material, mineral oil, or other fermentable materials can be used as the fermentation substrate in a fermentation stage in methods of the present invention. The fermentable material can be biomass. The term "biomass" can refer generally to organic matter harvested or collected from a renewable biological resource as a source of energy. The renewable biological resource can include plant materials (e.g., plant biomass), animal materials, and/or materials produced biologically. The term "biomass" is not considered to include non-renewable fossil fuels, such as coal, petroleum, and/or natural gas, which do not normally include glycerides (e.g., tri-, di-, mono-).

As indicated, the nutrient composition of the present invention combines at least corn steep liquor and at least one other component that is at least one antifoaming agent, or at least one surfactant, or any combination thereof. As indicated, both at least one antifoaming agent and at least one surfactant can be included in the combination.

As used herein, "corn steep liquor" refers to a by-product of corn wet-milling. Corn steep liquor is a mixture formed of the water soluble extracts of corn soaked (steeped) in water. Approximately half of corn steep liquor is water, with the remainder composed of natural nutritive materials such as crude proteins, amino acids, minerals, vitamins, reducing sugars, organic acids, enzymes and other elemental nutrients. Corn steep liquor provides a rich source of microbial nutrients. Corn steep liquor is assigned CAS No. 66071-94-1. While the actual percent composition of a corn steep liquor may vary somewhat between manufacturers, Table I lists an average composition of major constituents of an example of corn steep liquor. Other corn steep liquor compositions may be used.

TABLE I

| Corn Steep Liquor Composition, Major Component | Percent Composition, wt % |
|---|---|
| Ash (oxide) | 15-19 |
| Crude Protein | 45-49 |
| Fat | 0.3-0.5 |
| Lactic Acid | 24-28 |
| Nitrogen | 7-8 |
| Phytic Acid | 7.3-8.3 |
| Reducing Sugars (as dextrose) | 2-3 |
| Water | amount to bring total composition to 100%, e.g., 45-50 |

Corn steep liquor can be obtained from commercial milling companies or obtained directly by wet milling corn. The corn wet milling process usually begins with corn that has been removed from the cobs and cleared of all debris and foreign materials. The milled corn enters a steeping stage, where the kernels are soaked in heated water that can be mildly acidic (e.g., from sulfur dioxide addition to the water) with the water maintained, for instance, at about 45-54° C. (or other temperature), and steeping is continued normally for about 20-50 hours (or other amount of time), while the corn usually is moved through successive steeping tanks. Water can be absorbed by the corn (e.g., approximately one-third of the water may be absorbed by the corn) during the steeping, and the remaining amount (e.g., other approximate two-thirds) can be withdrawn from the steeping system as light steepwater that contains solids, such as from 5-10% solids by weight. The light steepwater can then be evaporated, for instance until it contains from 40-60% solids, usually about 45% to about 50% solids, to provide corn steep liquor.

When added to a culture medium as part of a nutrient composition of the present invention, corn steep liquor can be included in the culture medium in a concentration of from about 0.05% (w/v) to about 20.00% (w/v), or from about 0.10% (w/v) to about 10.00% (w/v), or from about 1.00% (w/v) to about 5.00% (w/v), based on solid (non-water) contents of the corn steep liquor and volume of the treated culture medium.

As used herein, an "antifoaming agent" is a surfactant/wetting agent which additionally has foam-breaking effects, or foam-inhibiting effects, or both, with respect to a culture medium, such as a culture medium used for cell propagation or fermentation. The antifoaming agent can improve oxygen transfer rate across the fermentation media and yeast cell membrane. The antifoaming agent can be an organic antifoaming agent(s) and/or an inorganic antifoaming agent. The organic antifoaming agent can be a polyglycol, a blend of polyglycol and silicone, a fatty acid ethoxylate, an ethoxylated fatty amine, or any combination thereof.

The antifoaming agent, including the organic antifoaming agent, can have an HLB value of from about 1 to about 5, or an HLB value of from about 1 to about 4, or an HLB value of from about 2 to about 4, or an HLB value of from about 2 to about 3, or other values. It is common to characterize surface active additives by a hydrophile-lipophile balance value, also known as HLB value. The HLB value can be calculated in a conventional manner. For example, the HLB value of a surface active agent can be calculated by dividing the molecular weight percent of the hydrophilic portion of the surface active agent by five. For example, a surfactant/wetting agent containing 20 mole % hydrophilic portion (total) would have an HLB value calculated to be 4 (i.e., 20/5=4). HLB values that exceed 20 are relative or comparative values. Additives with a low HLB are more lipid loving while those with a high HLB are more hydrophilic.

The organic antifoaming agent can comprise a blend of polyglycol and silicone. The polyglycol can be polyethylene glycols (PEGs), methoxypolyethylene glycols (MPEGs), polypropylene glycols (PPGs), polybutylene glycols (PBGs), polyglycol copolymers, or others, which can be used in a single kind or any combinations thereof. PEGs may be used that have an average molecular weight of from about 500 to about 8000 or other values. PEGs are commercially available, such as CARBOWAX products from Dow Chemical Company. Silicones are polymers that include repeating units of siloxane, which is a functional group with the structure Si—O—Si. As an option, silicones are mixed inorganic-organic polymers with the chemical formula $[R_2SiO]_n$, where R is an organic group such as methyl, ethyl, or phenyl, and these materials have the siloxane backbone chain ( . . . Si—O—Si—O—Si—O— . . . ) with organic side groups attached to the silicon atoms. The silicone can be a polydimethyl siloxane, such as linear polydiemthylsiloxane (PDMS), a silicone oil. The polydimethylsiloxane oil may be selected from those having a viscosity average of from about 200 to about 750 cSt (25° C.) and an average molecular weight (Da) of from about 10,000 to about 50,000. The silicone may be a reaction product of a siloxane with a silica. The polyglycol and polysilicone can be completely soluble in water. The blend of polyglycol and silicone may be prepared as an aqueous solution with the weight ratios of polydimethylsiloxane to polyglycol ranging from about 2:3 to about 1:1, or about 4:5. The total solids content of the aqueous solution comprised of polyglycol and silicone can be from about 1 wt % to about 25 wt %, or other values, based on the solution. A blend of polyglycol can be commercially obtained from Dow Chemical Company, Ivanhoe Industries, or Clariant Chemicals.

When added to a culture medium as part of a nutrient composition of the present invention, the antifoaming agent, such as the organic antifoaming agent, can be included in the culture medium in a concentration of from about 0.001% (w/v) to about 5.0% (w/v), or from about 0.005% (w/v) to about 4.0% (w/v), or from about 0.010% (w/v) to about 3.0% (w/v), based on solid (non-water) contents of the antifoaming agent and volume of the treated culture medium.

As used herein, a "surfactant" is a compound that lowers the surface tension (or interfacial tension) between two liquids or between a liquid and a solid in a culture medium. Surfactants may act as detergents, wetting agents, emulsifiers, or dispersants in a culture medium. The surfactant can be a nonionic or amphoteric surfactant. Where a nutrient composition is described herein as containing both the antifoaming agent (e.g., the organic antifoaming agent) and a surfactant, these two materials are different kinds of compounds or compositions. For example, the organic antifoaming agent can be a surfactant/wetting agent that is a different compound from the surfactant compound used in the same nutrient composition. This compositional difference can be further reflected by a difference in their properties, such as their respective HLB values.

As used herein, a "nonionic surfactant" is an organic compound that is amphiphilic and has no charge group at either terminal end group thereof, wherein the organic compound can lower the surface tension of a liquid, the interfacial tension between two liquids, or that between a liquid and a solid. The nonionic surfactant can be an ethoxylated sorbitan ester, a glyceride ethoxylate, an ethoxylated castor oil, an alcohol ethoxylate, an alkylphenol ethoxylate, a phenol ethoxylate, an amide ethoxylate, a fatty acid ethoxylate, a fatty amine ethoxylate, a fatty amide ethoxylate, a fatty mono or di-ethanolamide, an alkyl glycoside, a polyethylene glycol (PEG), an acetylenic glycol, a polypropylene glycol (PPG), a poloxamer, an alkali metal arylsulfonate, an ethoxylated fatty amide, or any combination thereof. As an option, the nonionic surfactant can be an ethoxylated sorbitan ester. The ethoxylated sorbitan esters can be commercially obtained as TWEEN or polysorbate series surfactant, such as polysorbate (80) (e.g., (TWEEN 80), polysorbate (20) (e.g., TWEEN 20), polysorbate (40) (e.g., TWEEN 40), or polysorbate 60 (e.g., TWEEN 60). TWEEN 80 is (polyoxyethylene (20) sorbitan monooleate. TWEEN 80, or other nonionic surfactants such as described herein, can improve the tolerance of yeast cells to high ethanol concentration. Commercial sources of the nonionic surfactant, such as polysorbates, which can be used in a nutrient composition of the present invention include, for example, Lumisorb Polysorbates from Lambent Technologies Corporation (Gurnee, Ill. USA). Other suitable nonionic surfactants are ethoxylated castor oils such as castor oil 80 EO. Poloxamers can be nonionic triblock copolymers that comprise a central block of a hydrophobic polyalkyleneoxide block, which is flanked on both sides with hydrophilic polyalkyleneoxide blocks. Poloxamers are commercially available that are food grade. A commercial source of poloxamers are, for example, PLURONIC copolymers from BASF Corporation (Florham Park, N.J., U.S.A.). Other suitable nonionic surfactants are mono-, di- or triglycerides based on fatty acids having 12-22 carbon atoms, or mono-, di- or triesters of sorbitan based on fatty acids having 12-22 carbon atoms. The nonionic surfactant can be used in the nutrient composition in a single type or a combination of two or more surfactants.

The surfactant, including the nonionic surfactant, can have an HLB value of from about 2 to about 39, or an HLB value of from about 7 to about 25, or an HLB value of from about 10 to about 20, or an HLB value of from about 12 to about 18, or an HLB value of from about 14 to about 16, or an HLB value of about 15, or other values. When combinations of different surfactants are used, the weighted average of the individual surfactant components can be used to calculate the HLB of the combination.

As used herein, "amphoteric surfactants" have both cationic and anionic centers attached to the same molecule. The cationic part can be based on primary, secondary, or tertiary amines or quaternary ammonium cations. The anionic part can be more variable and may include sulfonates. The amphoteric surfactants can be of betaine type, such as cococamidopropyl betaine or alkyl dimethyl betaine, or of oxido type, such as alkyl dimethyl amine oxido, for example.

When added to a culture medium as part of a nutrient composition of the present invention, the surfactant, such as the nonionic surfactant, can be included in the culture medium in a concentration of from about 0.005% (w/v) to about 5.0% (w/v), or from about 0.01% (w/v) to about 4.0% (w/v), or from about 0.10% (w/v) to about 3.0% (w/v), based on solid (non-water) contents of the surfactant and volume of the treated culture medium.

These two or three components of the nutrient composition can be added to a growth medium from a single (pre-blended) package or can be added individually to provide the nutrient composition in situ in the culture medium treated with the nutrient composition. When pre-combined, the components of the nutrient composition can be formulated as an aqueous-based composition wherein the corn steep liquor and at least the antifoaming agent are dispersed or dissolved therein. The surfactant can be included in this aqueous-based composition. The nutrient composition can be in a form that permits it to be readily dispersed in a culture medium, such as with agitation, stirring, or other mixing action.

The nutrient composition can comprise from about 1.0% to about 99.9% by weight of the corn steep liquor, and at least one of (a) from about 0.1% to about 50% by weight of the at least one antifoaming agent, or (b) from about 0.1% to about 50% by weight of the at least one surfactant, or any combination of (a) and (b), based on total solids weight of the composition. As an option, the nutrient composition can comprise from about 1.0% to about 99.9% by weight of the corn steep liquor, from about 0.1% to about 50% by weight of the at least one antifoaming agent, and (if also included) from about 0.1% to about 50% by weight of the at least one surfactant, based on total solids weight of the composition. As a specific option, the nutrient composition can comprise from about 95.0% to about 99.0% by weight of the corn steep liquor, and at least one of (a) from about 1.0% to about 5.0% by weight of the at least one antifoaming agent, or (b) from about 1.0% to about 5.0% by weight of the at least one surfactant, or any combination of (a) and (b), based on total solids weight of the composition. As a specific option, the nutrient composition can comprise from about 95.0% to about 99.0% by weight of the corn steep liquor, from about 1.0% to about 5.0% by weight of the at least one antifoaming agent, and from about 1.0% to about 5.0% by weight of the at least one surfactant, based on total solids weight of the composition. As a more specific option, the nutrient composition can comprise from about 96.0% to about 99.0% by weight of the corn steep liquor, and from about 1.0% to about 4.0% by weight of the at least one antifoaming agent. As a more specific option, the nutrient composition can comprise from about 94.0% to about 99.0% by weight of the corn steep liquor and from about 1.0% to about 6.0% by weight of the at least one surfactant, based on total solids weight of the composition. As a more specific option, the nutrient composition can comprise from about 97.0% to about 99.0% by weight of the corn steep liquor, and at least one of (a) from about 1.0% to about 3.0% by weight of the at least one antifoaming agent, or (b) from about 1.0% to about 3.0% by weight of the at least one surfactant, or any combination of (a) and (b), based on total solids weight of the composition. As a more specific option, the nutrient composition can comprise from about 97.0% to about 99.0% by weight of the corn steep liquor, from about 1.0% to about 3.0% by weight of the at least one antifoaming agent, and from about 1.0% to about 3.0% by weight of the at least one surfactant, based on total solids weight of the composition.

Additional ingredients may be included in the nutrient composition provided that the additional ingredients do not affect the yeasts thereby damaging the fermentation process. The nutrient composition can be introduced in the fermentation process to be treated by any conventional means.

The yeast that can be used in the culturing and fermenting steps can be any yeast used in fermenting. Examples include *Saccharomyces cerevisiae, Saccharomyces pastorianus (carlsbergiensis), Kluyveromyces lactis, Kluyveromyces fragilis, Fusarium oxysporum*, or any combination thereof. Culturing and fermenting can be performed using a mixture containing from about 0.01% to about 50.00% by weight of at least one yeast and from about 99.99% to about 50.00% by weight of the nutrient composition, or using a mixture containing from about 0.10% to about 25.0% by weight of at least one yeast and from about 0.10% to about 10.0% by weight of the nutrient composition, or other mixing amounts.

Figure 1B:
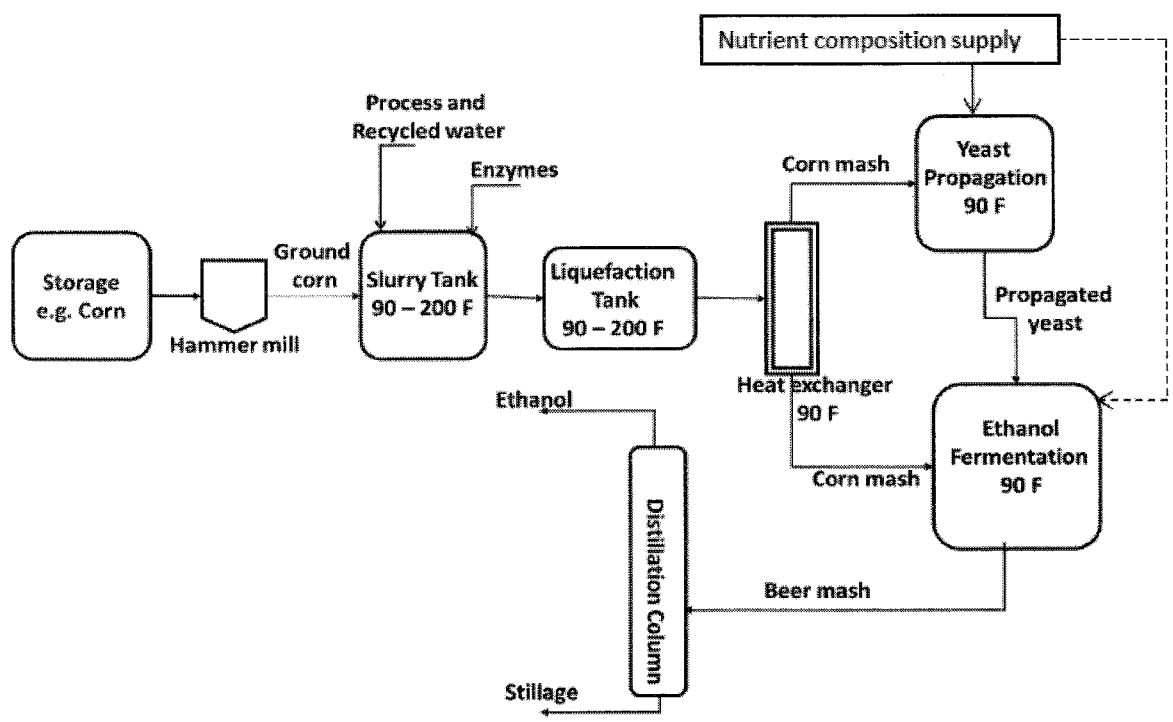
FIG. 1B illustrates a process flow diagram of a method of corn ethanol production in a production plant with introduction of a propagated yeast which is prepared using a nutrient composition according to an example of the present invention.

The nutrient composition of the present invention can be used in laboratory scale cell culturing and fermentation, and/or in industrial scale ethanol fermentation, such as in an ethanol production plant. Referring to FIG. 1B, the process flow diagram shows a method of ethanol production in a corn ethanol production plant with introduction of a propagated yeast according to an example of the present invention. As indicated in the figure, a nutrient composition of the present invention can be added in the culturing used to provide the propagated yeast, and as an option, also can be added, in ethanol fermentation. The nutrient composition is illustrated in this example as added to yeast propagation and optionally ethanol fermentation as a single preformed mixture of its components (corn steep liquor, antifoaming agent, and, if also included, surfactant) to simplify the illustration. The processing equipment and lay-out thereof, materials, and reaction conditions indicated in FIG. 1B are provided as examples only and are not necessarily limiting. As indicated, the constituents of the nutrient composition may be added individually or in subcombinations thereof, or in precombinations with other additives, to the process units/stages such as the culturing stages. Other materials and additives not shown in the figure optionally may be added, such as in a yeast propagation recipe used in yeast propagation, in an ethanol fermentation recipe used in ethanol fermentation, or in both or other process stages or units. An industrial scale ethanol fermentation in an ethanol production plant can have processes and systems such as described in the U.S. Patent Application Publication No. 2011/0230394 A1, which is incorporated herein in its entirety by reference. Nutrient compositions of the present invention can be used with fermentation substrates that comprise grains such as corn, wheat, rye, barley and sorghum, lignocellulosic materials such as wood, willow and switch grass, agricultural residues such as corn stover, corn cobs, straw and bagasse, sugar cane, molasses, sugar beet, starch materials such as tapioca (cassava) and potatoes, paper and pulp mills waste, algae, wood, seeds, or grasses, or other fermentable substrates, or any combination thereof. Ethanol fermentations that can be supported by the nutrient compositions of the present invention can include those directed to processing of corn to ethanol, sugar cane to ethanol, dry grind ethanol, wet grain ethanol, wheat to ethanol, barley to ethanol, oats to ethanol, rye to ethanol, sorghum to ethanol, cellulosic to ethanol, sugar beet to ethanol, rice to ethanol, brewing operations, and others. In addition to the ethanol fermentations illustrated herein, the nutrient composition of the present invention can be used in other kinds of fermentations, such as microbial enzyme fermentation, vitamin fermentation, antibiotics fermentation, amino acids fermentation, organic acids fermentation, butanol fermentation, xylitol fermentation, flavorings fermentation, beer fermentation, wine fermentation, or other fermentations. The nutrient composition of the present invention may be used in lactic acid fermentations (e.g., homolactic or heterolactic or malolactic fermentation) or other kinds of fermentations.

The addition of the nutrient composition can result in an increased yeast concentration in a propagated yeast culture, such as at least about 3 million cells per gram, or at least about 4 million cells per gram, or at least about 5 million cells per gram, or at least about 6 million cells per gram, or from about 6 to about 27 million cells per gram, or more, as compared to a yeast concentration in the propagated yeast culture wherein the culturing is done with the addition of only the corn steep liquor (same amount) and without the antifoaming agent (or without the antifoaming agent and the surfactant). The addition of the nutrient composition can result in an increased yeast concentration in the propagated yeast culture of at least about 25% more on a cells per unit weight basis (or at least about 5% more on a cells per unit volume basis) as compared to a yeast concentration in the propagated yeast culture wherein the culturing is done with addition of only the corn steep liquor (same amount) and without the antifoaming agent (or without the antifoaming agent and the surfactant). Addition of the nutrient composition can result in an increased ethanol concentration in the fermented biomass of at least 1% w/v as compared to an ethanol concentration in the propagation and fermentation tanks wherein the culturing is done with addition of only the corn steep liquor (same amount) and without the antifoaming agent and surfactant. When fermenting is a high gravity fermentation, e.g., at from 30% to 40% fermentable solids, addition of the nutrient composition can result in an increased ethanol yield of at least about 2% as compared to the ethanol yield wherein the culturing is done with a same amount of urea in place of the nutrient composition. When propagation and fermentation tanks comprise an ethanol concentration of from about 0.02% to about 18% w/v, addition of the nutrient composition can result in an increased yeast concentration in the fermented biomass of at least about 2.5% on a cells per unit weight basis as compared to a yeast concentration in the fermented biomass wherein the culturing is done with addition of only the corn steep liquor (same amount) and without the antifoaming agent (or without the antifoaming agent and the surfactant). Addition of the nutrient composition can result in decreased residual sugar concentration in the fermented biomass of at least 3% w/v as compared to a residual sugar concentration in the propagation and fermentation tanks where the culturing is done with addition of only the corn steep liquor (same amount) and without the antifoaming agent.

The present invention will be further clarified by the following examples, which are intended to be purely exemplary of the present invention, in which parts are proportions by weight unless otherwise specified.

EXAMPLES

In the Examples, several variations of the present invention were tested and compared with comparative treatments or controls.

Testing Procedure:

Experimental evaluations were conducted for nutrient product compositions that contained one or combinations of three components. These three components included:

Corn steep liquor: obtained as a by-product of corn wet-milling in the form of a viscous concentrate of corn solubles (Solulys 048K from Roquette America Inc.).

Surfactant: TWEEN 80 (polyoxyethylene (20) sorbitan monooleate, commercially obtained from Harcross Chemicals, Ivanhoe Industries, Inc., Dow Chemicals, or BASF).

Organic antifoaming agent (XFO-12A), which is a blend comprising polyglycol and silicone, commercially obtained from Ivanhoe Industries, or Clariant.

In the examples described herein, these components were formulated singly or in different combinations to different levels and the resulting nutrient compositions were evaluated following a typical corn ethanol plant recipe with the nutrient compositions added as a replacement of urea in the recipe, the currently used source of nitrogen, unless otherwise indicated. The corn ethanol plant recipe used in the examples described herein used the following materials and laboratory procedures, wherein the corn ethanol plant recipe used for yeast cell count tests was the Yeast Propagation Recipe described below, and the corn ethanol plant recipe used for the ethanol fermentation tests was the Ethanol Fermentation Recipe described below:

| Yeast Propagation Recipe | |
|---|---|
| Item | Composition, % wt/vol |
| Corn mash | 73.770 |
| Process Water | 25.989 |
| Dry yeast | 0.061 |
| Gluco amylase enzyme | 0.012 |
| Alpha amylase enzyme | 0.012 |
| Protease enzyme | 0.018 |
| Antibiotics | 0.002 |
| Nutrient Composition (Examples: XP1, XP3-XP11) | 0.138 |

| Ethanol Fermentation Recipe | |
|---|---|
| Total working Volume | Composition, % wt/vol |
| Corn mash | 97.7594 |
| Gluco amylase enzyme | 0.0294 |
| Alpha amylase enzyme | 0.0015 |
| Protease enzyme | 0.001 |
| Anibiotics | 0.0001 |
| Propagated yeast contents | 2.1500 |
| Nutrient composition (Examples: XP1, XP3-XP11) | 0.0584 |

The Ethanol Fermentation Recipe contained a % of the Yeast Propagation from the Yeast Propagation Recipe as indicated, besides a separate amount of the nutrient composition. In the examples herein, the various nutrient compositions were evaluated for yeast cell count, yeast cell concentration increases, such as a measure of increased yeast cell viability, yeast cell vitality, and/or yeast cell budding; ethanol production; ethanol production with high gravity fermentation; high ethanol concentration tolerance; and residual sugars.

The evaluated nutrient compositions that were used in the examples are described in the following Table 1 and Table 2.

TABLE 1

| Nutrient Composition Identifier | Component(s) |
|---|---|
| XP1 | Corn steep liquor |
| XP3 | Corn steep liquor and antifoaming agent |
| XP4 | Corn steep liquor, antifoaming agent, and surfactant |

TABLE 2

| | Composition, wt % | | |
|---|---|---|---|
| Component | XP1 | XP3 | XP4 |
| Corn steep liquor | 100.00 | 98.00 | 96.00 |
| Antifoaming Agent | 0.00 | 2.00 | 2.00 |
| Surfactant | 0.00 | 0.00 | 4.00 |

Example 1

Yeast Cell Growth

Different nutrient compositions were evaluated using the indicated corn ethanol plant recipe (Yeast Propagation Recipe) to compare the effects on yeast cell growth by use of corn steep liquor in combination with the antifoaming agent, and separately in combination with the antifoaming agent and the surfactant, in comparison to the use of corn steep liquor only.

Yeast cell counts were determined by Hemocytometer and Cellometer methods.

Figure 2:
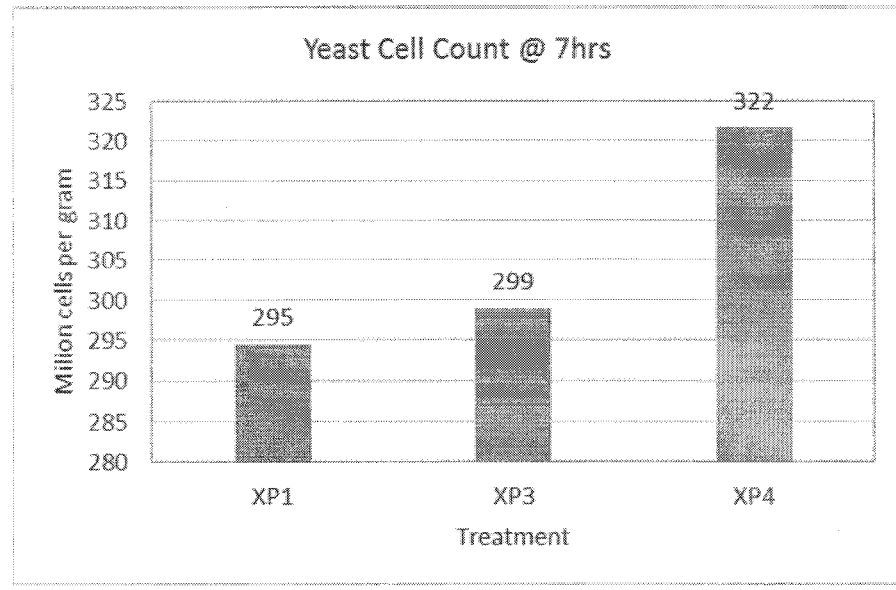
FIG. 2 is a bar graph depicting the effects on yeast cell count concentration obtained from different nutrient compositions that were used in a cell propagating experiment, wherein a comparison composition contained corn steep liquor only ("XP1"), and compositions according to examples of the present invention contained corn steep liquor and an antifoaming agent in one formulation ("XP3"), and corn steep liquor, an antifoaming agent, and a surfactant in another formulation ("XP4").

FIG. 2 is a bar graph depicting the effects on yeast cell count concentration obtained from different nutrient compositions that were used in this cell propagating experiment. The comparison composition contained corn steep liquor only ("XP1"), and the compositions representing examples of the present invention contained corn steep liquor and an antifoaming agent in one formulation ("XP3"), and corn steep liquor, an antifoaming agent, and a surfactant in another formulation ("XP4").

As shown by the results in FIG. 2, addition of antifoaming agent (XP3), and addition of antifoaming agent and surfactant 80 (XP4), to corn steep liquor (XP1), led to an increase in yeast cell count by an average of 6-27 million cells per gram. This trend has been observed for all experiments run in this study.

Example 2

Ethanol Production

Different nutrient compositions were evaluated using the indicated corn ethanol plant recipe (Ethanol Fermentation Recipe) to compare the effects on ethanol production by use of corn steep liquor in combination with the antifoaming agent, and separately in combination with the antifoaming agent and the surfactant, in comparison to the use of corn steep liquor only.

Ethanol concentrations (wt %) were determined by high-performance liquid chromatography (HPLC) method.

Figure 3:
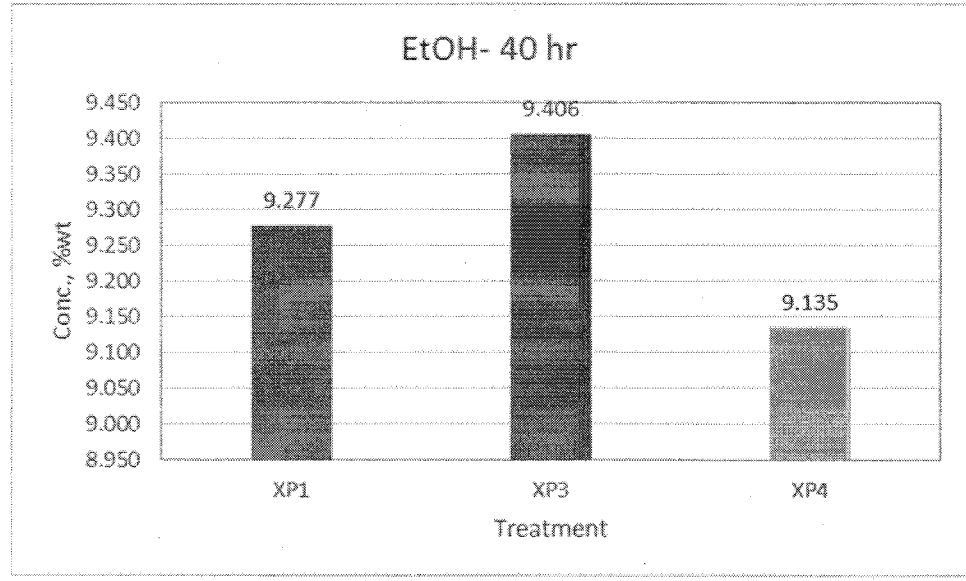
FIG. 3 is a bar graph depicting the effects on ethanol concentration obtained from different nutrient compositions that were used in a fermentation experiment, wherein a comparison composition contained corn steep liquor only ("XP1"), and compositions according to examples of the present invention contained corn steep liquor and an antifoaming agent in one formulation ("XP3"), and corn steep liquor, an antifoaming agent, and a surfactant in another formulation ("XP4").

FIG. 3 is a bar graph depicting the effects on ethanol concentration obtained from different nutrient compositions that were used in this fermentation experiment, wherein a comparison composition contained corn steep liquor only ("XP1"), and compositions representing examples of the present invention contained corn steep liquor and an antifoaming agent in one formulation ("XP3"), and corn steep liquor, an antifoaming agent, and a surfactant in another formulation ("XP4").

As shown by the results in FIG. 3, product XP3 formulated with corn steep liquor and antifoaming agent led to an average of 1.39% increase in ethanol concentration compared to XP1 formulated with only corn steep liquor. The significance of this result can be better appreciated by considering that there is a big vessel fermentation volume of 800,000 gallons for a typical 100 million gallons per year bioethanol plant. In that scale of operation, an increase of 1.39% ethanol concentration would lead to an additional 1.39 million gallons of ethanol product, which would generate significant additional revenue.

XP3 product has consistently shown an increase in ethanol production throughout this study registering up to more than 3% increase in ethanol production. The XP4 product containing surfactant and antifoaming agent, though slightly lower in ethanol production from XP1 and XP3 in these experiments, still maintained satisfactory ethanol production rates exceeding 9% and did negatively impact the ethanol production, while being able to provide other advantages, such as indicated in Example 1.

Example 3

Ethanol Production with High Gravity Fermentation

Nutrient compositions were evaluated using the indicated corn ethanol plant recipe (Ethanol Fermentation Recipe) to compare the effects on ethanol production with high gravity fermentation by use of corn steep liquor in combination with the antifoaming agent, in comparison to the use of urea. Urea is the current source of nitrogen used in most corn ethanol plants.

High gravity fermentation refers to conducting the fermentations at from 30% to 40% fermentable solids. Ethanol concentrations (wt %) were determined in the same manner as the previous example.

For this high gravity fermentation study, the shake flasks contained 32-35% corn flour treated with urea at 600.00 mg/L in the culturing medium (referred to as "no dose" since it contains no corn steep liquor, antifoaming agent or surfactant) and two levels of product XP3 (Dose 1× & 2×). Dose 1× refers to the concentration of nutrient composition used in the base medium as indicated above in the testing procedure. Dose 2× refers to use of twice as much nutrient composition in the base medium.

Figure 4:
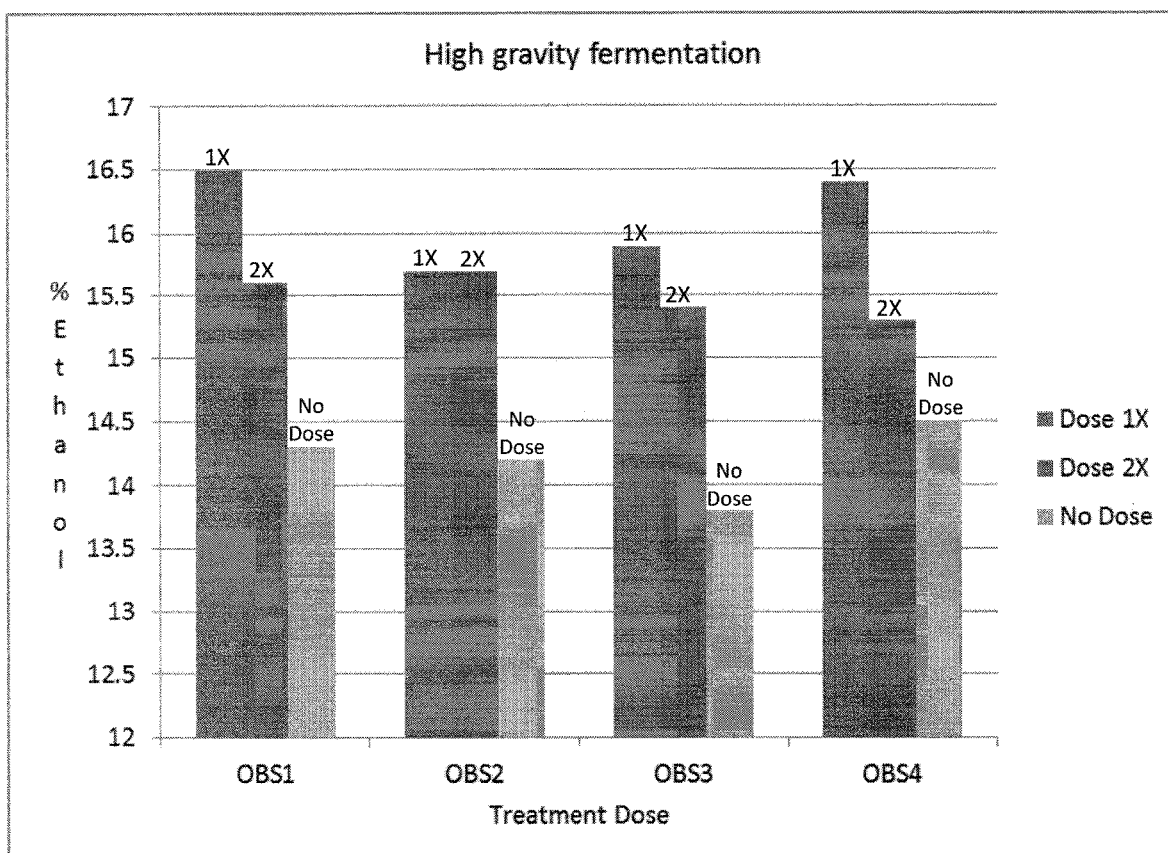
FIG. 4 is a bar graph depicting the effects on ethanol production at high gravity fermentation conditions obtained from treatment of corn flour with different sources of nitrogen in a fermentation experiment run as four trials ("OBS1"-"OBS4"), wherein compositions that contained corn steep liquor and an antifoaming agent were added at two different dosages in samples of each trial with results shown for a first dosage as the left-hand side bar for each of "OBS1"-"OBS4" ("dose 1×"), the middle bar for a second dosage for each of "OBS1"-"OBS4" ("dose 2×"), according to examples of the present invention, and urea was used as the nitrogen source for comparison in one of the samples of each trial with results shown as the right-hand bar for each of "OBS1"-"OBS4" ("No dose", which refers to no corn steep liquor, antifoaming agent or surfactant).

FIG. 4 is a bar graph depicting the effects on ethanol production at high gravity fermentation conditions obtained from treatment of corn flour with different sources of nitrogen in a fermentation experiment run as four trials, identified as OBS1, OBS2, OBS3, and OBS4, wherein compositions that contained corn steep liquor and an antifoaming agent were added at two different dosages in samples of each trial with results shown as the middle bar for each of OBS1 to OBS4 (dose 2×) and the left-hand side bar for each of OBS1 to OBS4 (dose 1×), according to examples of the present invention, and was used as the nitrogen source in one of the samples of each trial with results shown as the right-hand bar for each of OBS1 to OBS4 ("No dose" of corn steep liquor and antifoaming agent) for comparison.

As it can be seen in FIG. 4, treatments with XP3 product led to about 2.5% higher ethanol production than urea treatments.

Example 4

High Ethanol Concentration Tolerance

The formulated nutrient compositions were evaluated for their capability to improve yeast cells ability to withstand high ethanol concentration.

Yeast cell concentrations were determined by Hemocytometer and cellometer method.

Figure 5:
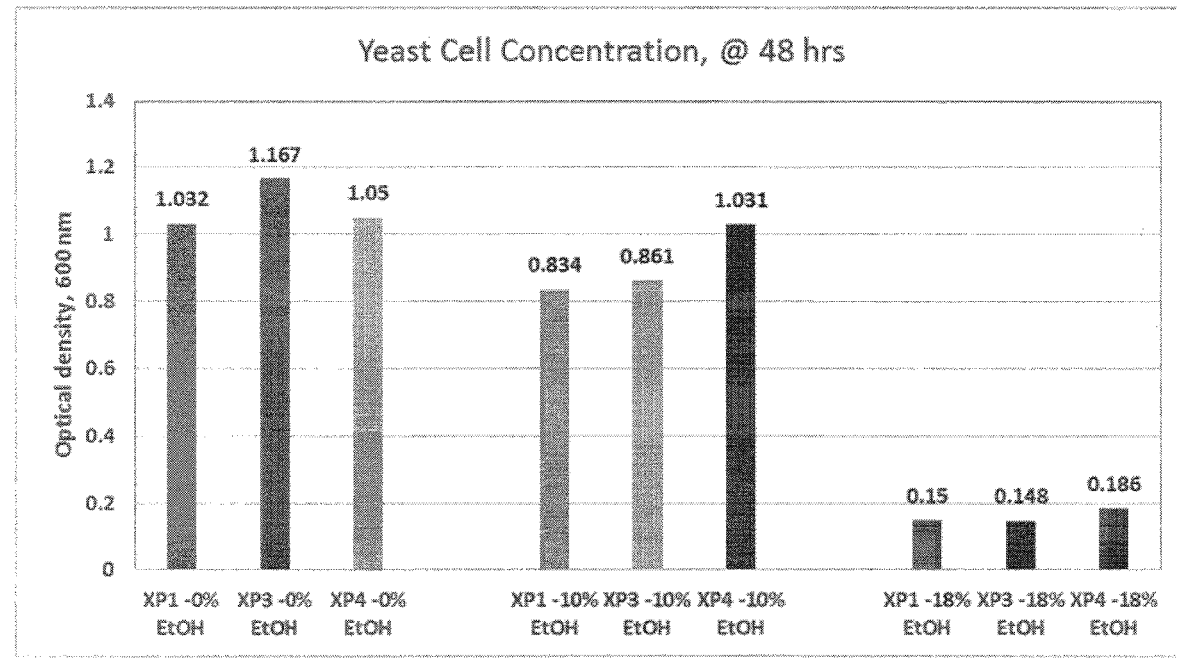
FIG. 5 is a bar graph depicting the effects on high ethanol concentration tolerance at three different ethanol concentrations (0%, 10%, and 18%) obtained from different nutrient compositions that were used in a cell propagating experiment, wherein comparison compositions contained corn steep liquor ("XP1"), and compositions according to examples of the present invention contained corn steep liquor and an antifoaming agent in one formulation ("XP3"), and corn steep liquor, an antifoaming agent, and a surfactant in another formulation ("XP4").

FIG. 5 is a bar graph depicting the effects on high ethanol concentration tolerance at three different ethanol concentrations (0 vol %, 10 vol %, and 18 vol %) obtained from different nutrient compositions that were used in this cell propagating experiment, wherein comparison compositions contained corn steep liquor (XP1), and compositions according to examples of the present invention contained corn steep liquor and an antifoaming agent in one formulation (XP3), and corn steep liquor, an antifoaming agent, and a surfactant in another formulation (XP4).

As it can be seen in FIG. 5, treatment with XP4 product showed higher yeast cell growth of over 10% compared to XP1 with fermentation media containing 10 vol % and 18 vol % ethanol concentration. Currently, most corn ethanol plants produce a maximum of about 14 vol % ethanol mainly because yeast cells can hardly survive in such high ethanol concentration environment. Improving the ability of yeast cells to withstand high ethanol concentration can be particularly more important as plants move into high gravity ethanol production technology.

Example 5

Sugar Utilization Rate

At the end of every fermentation cycle ethanol plant managers want to see very minimal residual sugars. Residual sugar level is another indicator of a good or bad run of fermentation. With minimal residual sugars a plant is expected to make more ethanol because it is presumed that yeast cells utilized the sugars to make a desired product (ethanol).

Different nutrient compositions were evaluated using the indicated corn ethanol plant recipe (Ethanol Fermentation Recipe) to compare the effects on residual sugars by use of corn steep liquor in combination with the antifoaming agent, and separately in combination with the antifoaming agent and surfactant, in comparison to the use of corn steep liquor only.

Total residual sugars were determined by HPLC method.

Figure 6:
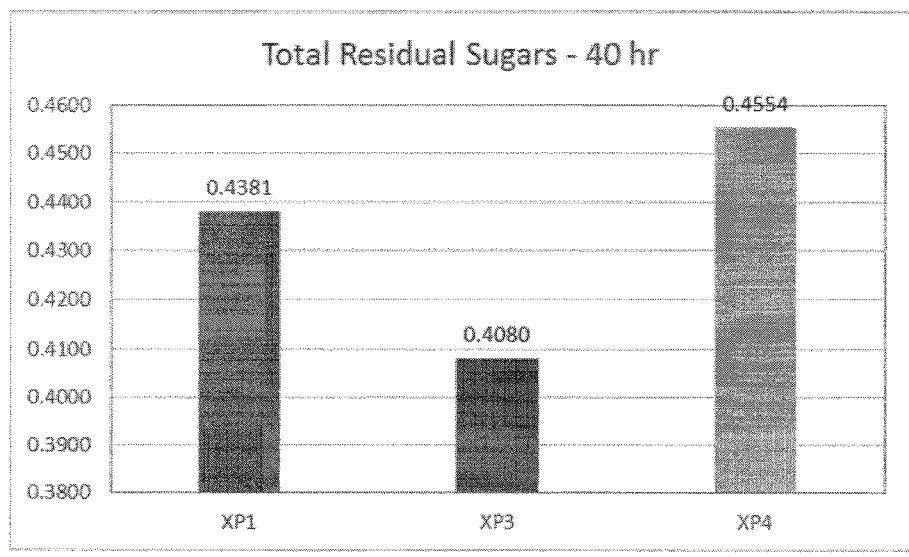
FIG. 6 is a bar graph depicting the effects on sugar utilization obtained from different nutrient compositions that were used in a fermentation experiment, wherein a comparison composition contained corn steep liquor only ("XP1"), and compositions according to the present invention contained corn steep liquor and an antifoaming agent in one formulation ("XP3"), and corn steep liquor, an antifoaming agent, and a surfactant in another formulation ("XP4"), wherein the results for these various compositions are depicted as total residual sugars in the figure.

FIG. 6 is a bar graph depicting the effects on sugar utilization obtained from different nutrient compositions that were used in this fermentation experiment, wherein a comparison composition contained corn steep liquor only (XP1), and compositions according examples of the present invention contained corn steep liquor and an antifoaming agent in one formulation (XP3), and corn steep liquor, an antifoaming agent, and a surfactant in another formulation (XP4), wherein the results for these various compositions are depicted as total residual sugars in the figure.

As shown by the results in FIG. 6, in this study, XP3 product treatment led to about 6.9% less residual sugars than XP1. This further shows better yeast cell growth and ethanol production observed with XP3 compared to XP1. XP4 had about 3.9% higher residual sugars than XP1.

The results in these examples show that a formulation of corn steep liquor with antifoaming agent, and in further combination with surfactant, can form a synergistic performance that benefits a corn ethanol fermentation process.

Example 6

Yeast Cell Growth

Additional different nutrient compositions were evaluated using the indicated corn ethanol plant recipe (Yeast Propagation Recipe) to compare the effects on yeast cell growth by use of corn steep liquor in combination with the antifoaming agent, and separately in combination with the surfactant, and separately in combination with the antifoaming agent and the surfactant, in comparison to the use of corn steep liquor only, antifoaming agent only, and surfactant only.

Yeast cell counts at 25 hours were determined by Hemocytometer and Cellometer methods.

Figure 7:
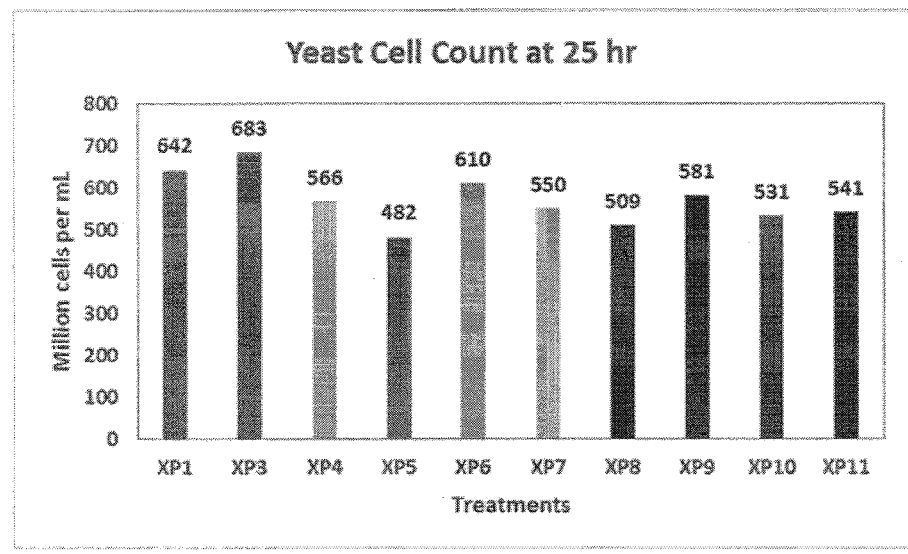
FIG. 7 is a bar graph depicting the effects on yeast cell count concentration obtained from different nutrient compositions that were used in a cell propagating experiment, wherein comparison compositions contained corn steep liquor only ("XP1"), or antifoaming agent only ("XP6"), or surfactant only ("XP9"), and compositions according to examples of the present invention which contained corn steep liquor and an antifoaming agent in different proportions in two formulations ("XP3", "XP5"), corn steep liquor and surfactant in different proportions in two formulations ("XP7", "XP8"), and corn steep liquor, an antifoaming agent, and a surfactant in different proportions in three other formulations ("XP4", "XP10", and "XP11").

FIG. 7 is a bar graph depicting the effects on yeast cell count concentration obtained from the ten additional different nutrient compositions that were used in this cell propagating experiment. The comparison compositions contained corn steep liquor only ("XP1"), or antifoaming agent only ("XP6"), or surfactant only ("XP9"), and compositions according to examples of the present invention which contained corn steep liquor and an antifoaming agent in different proportions in two formulations ("XP3", "XP5"), corn steep liquor and surfactant in different proportions in two formulations ("XP7", "XP8"), and corn steep liquor, an antifoaming agent, and a surfactant in different proportions in three other formulations ("XP4", "XP10", and "XP11").

The evaluated nutrient compositions of formulations XP1 and XP3 to XP11 that were used in this example are described in the following Table 3.

TABLE 3

| | Composition, wt % | | |
| --- | --- | --- | --- |
| Treatment | Corn steep liquor | Antifoaming agent | Surfactant |
| XP1 | 100.00 | 0.00 | 0.00 |
| XP3 | 98.00 | 2.00 | 0.00 |
| XP4 | 96.00 | 2.00 | 4.00 |
| XP5 | 95.00 | 5.00 | 0.00 |
| XP6 | 0.00 | 100.00 | 0.00 |
| XP7 | 98.00 | 0.00 | 2.00 |
| XP8 | 95.00 | 0.00 | 5.00 |
| XP9 | 0.00 | 0.00 | 100.00 |
| XP10 | 96.00 | 2.00 | 2.00 |
| XP11 | 96.00 | 3.00 | 1.00 |

As shown by the results in FIG. 7, the formulation XP3 of corn steep liquor (98%) and antifoaming agent (2%) led to the highest increase in yeast cell growth compared to all the treatments, and was 6.4% higher in yeast cell count compared to the treatment with corn steep liquor only formulation (XP1). The higher concentration of antifoaming agent (5%) with less corn steep liquor (95%) in formulation XP5 led to about a 25% decrease in yeast cell count relative to the results for the treatment using formulation XP1 (corn steep liquor only) and about a 29% decrease relative to product XP3 (98% corn steel liquor/2% antifoaming agent). This indicated that reduced yeast cell growth can result if the level of antifoaming agent is too high when used in combination with corn steep liquor (Table 3 and FIG. 7). The treatments with the formulations containing corn steep liquor and surfactant (XP7 and XP8) led to yeast cell counts that were reduced compared to the treatment with formulation containing corn steep liquor (XP1). Despite this, as indicated in the following Example 7, treatments with XP7 and XP8 can provide increased ethanol production compared to treatment with XP1. Treatments of formulations involving all the three components (i.e., corn steep liquor, antifoam and surfactant) in XP4, XP10, and XP11 also led to a drop in yeast cell count of over 11% compared to the treatment with corn steep liquor (XP1). Despite this, as indicated in Example 9, treatments with XP7 and XP8 can provide significantly reduced glycerol production compared to treatment with XP1.

Example 7

Ethanol Production

Additional different nutrient compositions were evaluated using the indicated corn ethanol plant recipe (Ethanol Fermentation Recipe) to compare the effects on ethanol production by use of corn steep liquor in combination with the antifoaming agent, and separately in combination with the antifoaming agent and the surfactant, in comparison to the use of corn steep liquor only, antifoaming agent only, and surfactant only.

Ethanol concentrations (wt %) at 64 hours were determined by high-performance liquid chromatography (HPLC) method.

Figure 8:
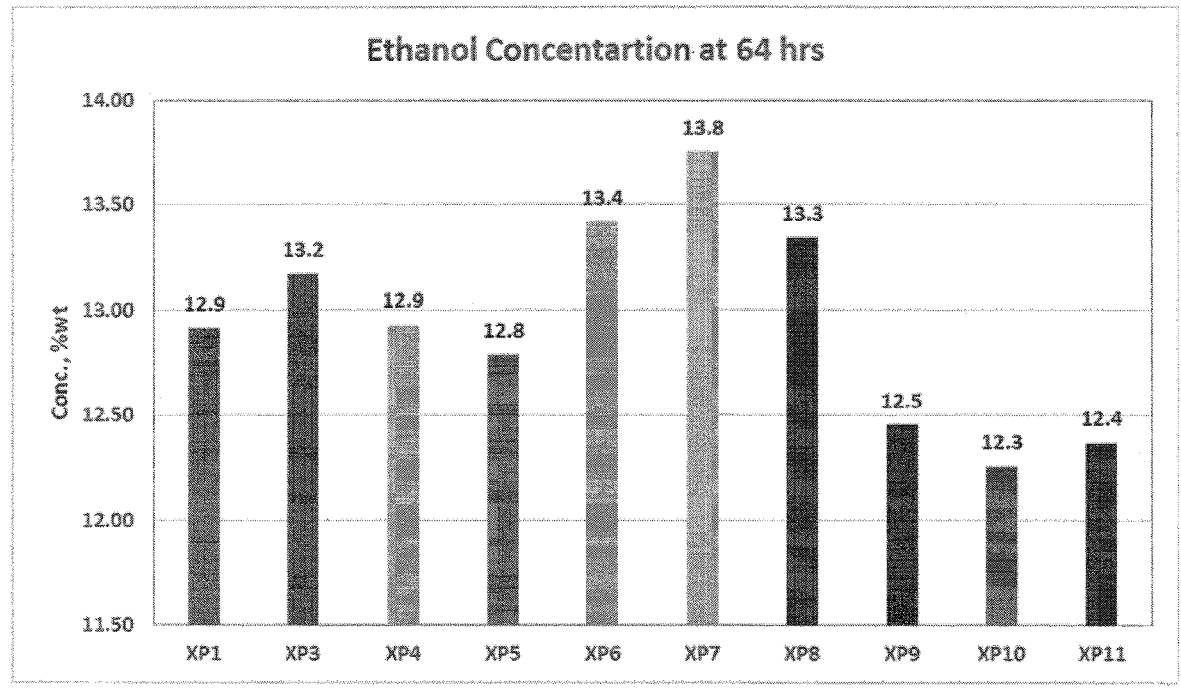
FIG. 8 is a bar graph depicting the effects on ethanol concentration obtained from different nutrient compositions that were used in a fermentation experiment, wherein comparison compositions contained corn steep liquor only ("XP1"), or antifoaming agent only ("XP6"), or surfactant only ("XP9"), and compositions according to examples of the present invention which contained corn steep liquor and an antifoaming agent in different proportions in two formulations ("XP3", "XP5"), corn steep liquor and surfactant in different proportions in two formulations ("XP7", "XP8"), and corn steep liquor, an antifoaming agent, and a surfactant in different proportions in three other formulations ("XP4", "XP10", and "XP11").

FIG. 8 is a bar graph depicting the effects on ethanol concentration obtained from different nutrient compositions that were used in this fermentation experiment, wherein the nutrient compositions corresponded to nutrient compositions XP1 and XP3-XP10 described in Table 3 in previous Example 6.

As shown by the results in FIG. 8, the use of treatments with formulations of surfactants and corn steep liquor (XP7 and XP8) led to the highest ethanol production increases among the evaluated formulations, as much as about 7% higher for treatment XP7 compared to treatment with the corn steep liquor (XP1). While not desiring to be bound to a specific theory, the presence of surfactant molecules can boost the yeast cells' ability to withstand high ethanol concentration environment and thus increase ethanol yield. Also, treatment with the formulation of corn steep liquor (98%) and antifoaming agent (2%) (Treatment XP3-13.2 wt % ethanol) led to slight increase in ethanol production compared to treatment with corn steep liquor (Treatment XP1-12.9 wt % ethanol). Addition of all three components (corn steep liquor, organic antifoaming agent, surfactant) led to the same or a drop in ethanol production (Treatments XP4-12.9 wt % ethanol, XP10-12.3 wt % ethanol, and XP11-12.4 wt % ethanol) compared to treatment with XP1.

These results showed that there is a synergy between corn steep liquor and antifoaming agent, and corn steep liquor and surfactant, in promoting corn ethanol production, whereas the presence of all three components provided ethanol production which was somewhat reduced.

Example 8

Sugar Utilization Rate

As indicated, the level of residual sugars is one of the indicators of the performance of a fermentation run. Low residual sugars indicate that there was a good yeast cell growth that consumed the sugars to produce a desired product.

Additional different nutrient compositions were evaluated using the indicated corn ethanol plant recipe (Ethanol Fermentation Recipe) to compare the effects on residual sugars by use of corn steep liquor in combination with the antifoaming agent, and separately in combination with the surfactant, and separately in combination with the antifoaming agent and surfactant, in comparison to the use of corn steep liquor only, antifoaming agent only, and surfactant only.

Total residual sugars at 64 hours were determined by HPLC method.

Figure 9:
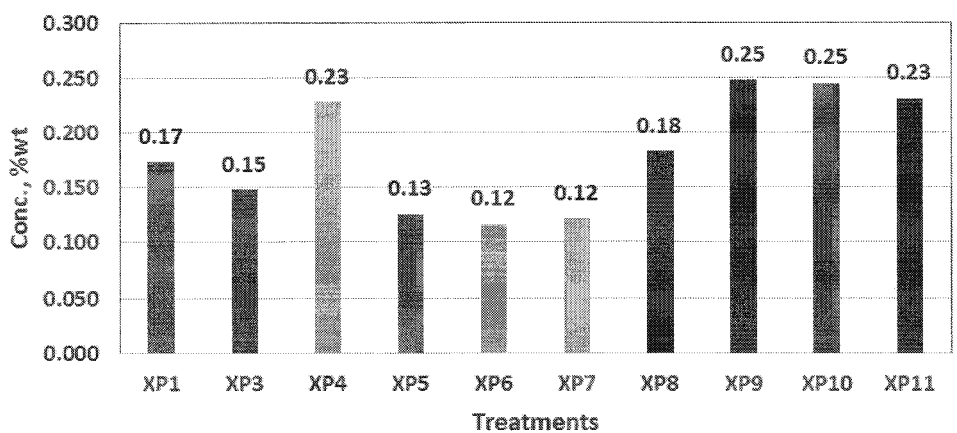
FIG. 9 is a bar graph depicting the effects on sugar utilization obtained from different nutrient compositions that were used in a fermentation experiment, wherein comparison compositions contained corn steep liquor only ("XP1"), or antifoaming agent only ("XP6"), or surfactant only ("XP9"), and compositions according to examples of the present invention which contained corn steep liquor and an antifoaming agent in different proportions in two formulations ("XP3", "XP5"), corn steep liquor and surfactant in different proportions in two formulations ("XP7", "XP8"), and corn steep liquor, an antifoaming agent, and a surfactant in different proportions in three other formulations ("XP4", "XP10", and "XP11"), wherein the results for these various compositions are depicted as total residual sugars in the figure.

FIG. 9 is a bar graph depicting the effects on sugar utilization obtained from different nutrient compositions that were used in this fermentation experiment, wherein the nutrient compositions corresponded to nutrient compositions XP1 and XP3-XP10 described in Table 3 in previous Example 6.

In this study, generally all treatments that had good cell growth had very low residual sugars at the end of fermentation. For instance, Treatment XP3, which had the highest yeast cell count in Example 6, had one of the lowest levels of residual sugars (0.15 wt %) compared to Treatment XP1 (0.17 wt %) residual sugars (FIG. 9). For treatments XP7 and XP8, which had high ethanol production in Example 7, treatment XP7 had lower residual sugar (0.12 wt %) and treatment XP8 had a residual sugar (0.18 wt %) comparable to that of Treatment XP1. These results further show the synergy between corn steep liquor and antifoaming agent, and between corn steep liquor and surfactant, in promoting yeast cell growth and health.

Example 9

Glycerol Production

The level of glycerol production in ethanol fermentation indicates the level of stress on yeast cells. Additional different nutrient compositions were evaluated using the indicated corn ethanol plant recipe (Ethanol Fermentation Recipe) to compare the effects on glycerol production by use of corn steep liquor in combination with the antifoaming agent, and separately in combination with the surfactant, and separately in combination with the antifoaming agent and surfactant, in comparison to the use of corn steep liquor only, antifoaming agent only, and surfactant only.

The glycerol content in the fermentation media can be determined by high performance liquid chromatography (HPLC) with a refractive index detector.

Figure 10:
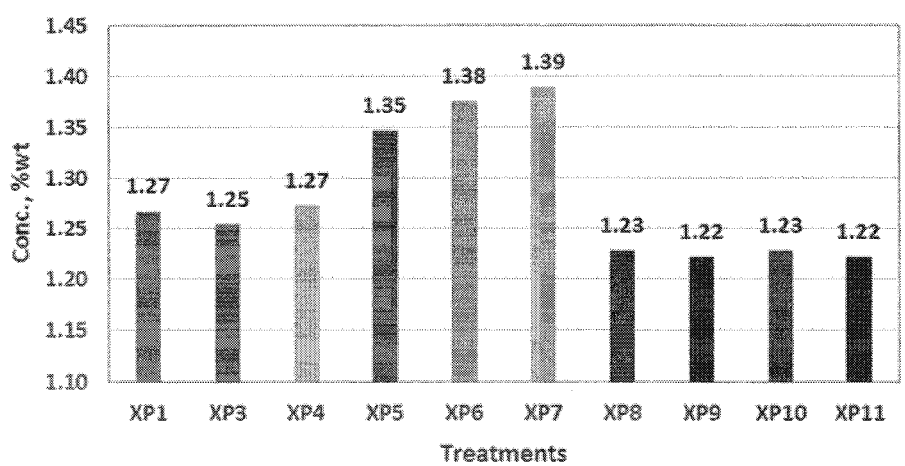
FIG. 10 is a bar graph depicting the effects on glycerol concentration obtained from different nutrient compositions that were used in a fermentation experiment, wherein comparison compositions contained corn steep liquor only ("XP1"), or antifoaming agent only ("XP6"), or surfactant only ("XP9"), and compositions according to examples of the present invention which contained corn steep liquor and an antifoaming agent in different proportions in two formulations ("XP3", "XP5"), corn steep liquor and surfactant in different proportions in two formulations ("XP7", "XP8"), and corn steep liquor, an antifoaming agent, and a surfactant in different proportions in three other formulations ("XP4", "XP10", and "XP11").

FIG. 10 is a bar graph depicting the effects on glycerol concentration obtained from different nutrient compositions that were used in this fermentation experiment, wherein the nutrient compositions corresponded to nutrient compositions XP1 and XP3-XP10 described in Table 3 in previous Example 6.

As shown in FIG. 10, the presence of corn steep liquor and antifoaming agent in the treatment with formulation XP3 led to a decrease in glycerol production compared to the treatment with corn steep liquor (XP1). The results for treatments with corn steep liquor and surfactant were mixed. The treatment with formulation XP7 (98% corn steep liquor+2% surfactant) led to higher glycerol production than corn steep liquor alone (XP1), whereas the treatment with corn steep liquor and surfactant of formulation XP8 (95% corn steep liquor+5% surfactant) led to lower glycerol production than treatment with corn steep liquor (XP1). These results showed that there is a synergy between corn steep liquor and antifoaming agent, and in at least some formulations of corn steep liquor and surfactant, in reducing glycerol production during corn ethanol fermentation.

The present invention includes the following aspects/embodiments/features in any order and/or in any combination:

1. The present invention relates to a method for enhancing yeast growth for bioproduct production, comprising:
   culturing at least one yeast in a growth medium containing a nutrient composition to obtain a propagated yeast culture, wherein the nutrient composition comprises corn steep liquor and at least one of (a) at least one antifoaming agent, or (b) at least one surfactant, or any combination thereof.

2. The method of any preceding or following embodiment/feature/aspect, wherein the nutrient composition comprises the at least one surfactant, such as a nonionic surfactant, an amphoteric surfactant, or any combination thereof.

3. The method of any preceding or following embodiment/feature/aspect, wherein the at least one antifoaming agent is present and is at least one organic antifoaming agent.

4. The method of any preceding or following embodiment/feature/aspect, wherein the at least one antifoaming agent is at least one surfactant that has an HLB value of from about 1 to about 5.

5. The method of any preceding or following embodiment/feature/aspect, wherein the at least one organic antifoaming agent is a polyglycol, a blend of polyglycol and silicone, a fatty acid ethoxylate, an ethoxylated fatty amine, or any combination thereof.

6. The method of any preceding or following embodiment/feature/aspect, wherein the at least one surfactant is a nonionic surfactant that is an ethoxylated sorbitan ester, a glyceride ethoxylate, an ethoxylated castor oil, an alcohol ethoxylate, an alkylphenol ethoxylate, a phenol ethoxylate, an amide ethoxylate, a fatty acid ethoxylate, a fatty amine ethoxylate, a fatty amide ethoxylate, a fatty mono or di-ethanolamide, an alkyl glycoside, a polyethylene glycol (PEG), an acetylenic glycol, a polypropylene glycol (PPG), a poloxamer, an alkali metal arylsulfonate, an ethoxylated fatty amide, or any combination thereof.

7. The method of any preceding or following embodiment/feature/aspect, wherein the at least one surfactant is a nonionic surfactant that is an ethoxylated sorbitan ester (polysorbate).

8. The method of any preceding or following embodiment/feature/aspect, wherein the at least one surfactant is a nonionic surfactant that has an HLB value of from about 2 to about 39.

9. The method of any preceding or following embodiment/feature/aspect, wherein the at least one surfactant is a nonionic surfactant that has an HLB value of from about 7 to about 25.

10. The method of any preceding or following embodiment/feature/aspect, wherein the nutrient composition comprises from about 1.0% to about 99.9% by weight of the corn steep liquor, at least one of (a) from about 0.1% to about 50% by weight of the at least one antifoaming agent, or (b) from 0% (or 0.1%) to about 50% by weight of the at least one surfactant, or any combination of (a) and (b), based on total solids weight of the composition.

11. The method of any preceding or following embodiment/feature/aspect, wherein the culturing comprises culturing a mixture containing from about 0.01% to about 50.00% by weight of the at least one yeast and from about 99.99% to about 50.00% by weight of the nutrient composition, based on the weight of the mixture.

12. The method of any preceding or following embodiment/feature/aspect, wherein the at least one yeast is *Saccharomyces cerevisiae, Saccharomyces pastorianus (carlsbergiensis), Kluyveromyces lactis, Kluyveromyces fragilis, Fusarium oxysporum*, or any combination thereof.
13. The method of any preceding or following embodiment/feature/aspect, wherein addition of the nutrient composition results in an increased yeast concentration in the propagated yeast culture of at least about 3 million cells per gram as compared to a yeast concentration in the propagated yeast culture wherein the culturing is done with addition of only the corn steep liquor and without the at least one antifoaming agent.
14. The method of any preceding or following embodiment/feature/aspect, wherein addition of the nutrient composition results in an increased yeast concentration in the propagated yeast culture of at least about 3 million cells per gram as compared to a yeast concentration in the propagated yeast culture wherein the culturing is done with addition of only the corn steep liquor and without the at least one surfactant and the at least one antifoaming agent.
15. The method of any preceding or following embodiment/feature/aspect, wherein addition of the nutrient composition results in an increased yeast concentration in the propagated yeast culture of at least about 25% more on a cells per unit weight basis as compared to a yeast concentration in the propagated yeast culture wherein the culturing is done with addition of only the same amount of said corn steep liquor and without the at least one antifoaming agent.
16. The method of any preceding or following embodiment/feature/aspect, wherein addition of the nutrient composition results in an increased yeast concentration in the propagated yeast culture of at least about 25% more on a cells per unit weight basis as compared to a yeast concentration in the propagated yeast culture wherein the culturing is done with addition of only the same amount of said corn steep liquor and without the at least one surfactant and the at least one antifoaming agent.
17. A method for fermentative bioproduct production, comprising:
culturing at least one yeast in a growth medium containing a nutrient composition to obtain a propagated yeast culture, wherein the nutrient composition comprises corn steep liquor and at least one of (a) at least one antifoaming agent, or (b) at least one surfactant, or any combination thereof;
inoculating a fermentation substrate with the propagated yeast culture to produce a fermentable biomass;
fermenting the fermentable biomass to produce a fermented biomass comprising at least one bioproduct and non-fermented solids content; and
separating at least a portion of the at least one bioproduct from the solids content.
18. The method of any preceding or following embodiment/feature/aspect, wherein the nutrient composition comprises the at least one surfactant, such as a nonionic surfactant, an amphoteric surfactant, or any combination thereof.
19. The method of any preceding or following embodiment/feature/aspect, wherein the corn steep liquor, the at least one antifoaming agent, and the at least one surfactant are premixed prior to addition for the culturing.
20. The method of any preceding or following embodiment/feature/aspect, wherein the corn steep liquor, the at least one antifoaming agent, and optionally the at least one surfactant are individually added for the culturing.
21. The method of any preceding or following embodiment/feature/aspect, wherein the at least one antifoaming agent is present and is at least one organic antifoaming agent.
22. The method of any preceding or following embodiment/feature/aspect, wherein the at least one antifoaming agent is a surfactant that has an HLB value of from about 1 to about 5.
23. The method of any preceding or following embodiment/feature/aspect, further comprising introducing additional nutrient composition comprising corn steep liquor, at least one antifoaming agent, and at least one surfactant, which is contained in the fermentable biomass.
24. The method of any preceding or following embodiment/feature/aspect, further comprising introducing additional nutrient composition comprising corn steep liquor, at least one antifoaming agent, and optionally at least one surfactant, which is contained in the fermentable biomass.
25. The method of any preceding or following embodiment/feature/aspect, wherein the corn steep liquor, the at least one antifoaming agent, and optionally the at least one surfactant are premixed prior to addition to the fermentable biomass.
26. The method of any preceding or following embodiment/feature/aspect, wherein the corn steep liquor, the at least one antifoaming agent, and optionally the at least one surfactant are individually added for the fermentable mass.
27. The method of any preceding or following embodiment/feature/aspect, wherein the at least one bioproduct is ethanol, oil, or a combination thereof.
28. The method of any preceding or following embodiment/feature/aspect, wherein the separating comprises a) distilling ethanol from the fermented biomass, b) extracting oil from the fermented biomass, or c) both a) and b).
29. The method of any preceding or following embodiment/feature/aspect, wherein addition of the nutrient composition results in an increased yeast concentration in the propagation and fermentation tanks of at least about 3 million cells per gram as compared to a yeast concentration in the propagation and fermentation tanks wherein the culturing is done with addition of only the same amount of said corn steep liquor and without the at least one antifoaming agent.
30. The method of any preceding or following embodiment/feature/aspect, wherein addition of the nutrient composition results in an increased yeast concentration in the propagation and fermentation tanks of at least about 3 million cells per gram as compared to a yeast concentration in the propagation and fermentation tanks wherein the culturing is done with addition of only the same amount of said corn steep liquor and without the at least one surfactant and the at least one antifoaming agent.
31. The method of any preceding or following embodiment/feature/aspect, wherein addition of the nutrient composition results in an increased ethanol concentration in the fermented biomass of at least 1% w/v as compared to an ethanol concentration in the propagation and fermentation tanks wherein the culturing is done with addition of only the same amount of corn steep liquor and without the at least one antifoaming agent and the at least one surfactant.
32. The method of any preceding or following embodiment/feature/aspect, wherein the fermenting is a high gravity fermentation at from 30% to 40% fermentable solids, and addition of the nutrient composition results in an increased ethanol yield of at least about 2% as compared to the ethanol yield wherein the culturing is done with a same amount of urea in place of the nutrient composition.

33. The method of any preceding or following embodiment/feature/aspect, wherein the propagation and fermentation tanks comprises an ethanol concentration of about 0.02% to about 18% w/v, and addition of the nutrient composition results in an increased yeast concentration in the fermented biomass of at least about 2.5% on a cells per unit weight basis as compared to a yeast concentration in the fermented biomass wherein the culturing is done with addition of only the same amount of said corn steep liquor and without the at least one surfactant and the at least one antifoaming agent.

34. The method of any preceding or following embodiment/feature/aspect, wherein addition of the nutrient composition results in decreased residual sugar concentration in the fermented biomass of at least 3% w/v as compared to a residual sugar concentration in the propagation and fermentation tanks wherein the culturing is done with addition of only the same amount of said corn steep liquor and without the at least one antifoaming agent.

35. The method of any preceding or following embodiment/feature/aspect, wherein culturing is performed in a fermentation mode selected from batch fermentation, fed-batch fermentation, or continuous fermentation.

36. The method of any preceding or following embodiment/feature/aspect, wherein fermenting is performed in a fermentation mode selected from batch fermentation, fed-batch fermentation, or continuous fermentation.

37. The method of any preceding or following embodiment/feature/aspect, wherein the fermentation substrate comprises grains such as corn, wheat, rye, barley and sorghum, lignocellulosic materials such as wood, willow and switch grass, agricultural residues such as corn stover, corn cobs, straw and bagasse, sugar cane, molasses, sugar beet, starch materials such as tapioca (cassava) and potatoes, paper and pulp mills waste, algae, wood, seeds, grasses, or any combination thereof.

38. The method of any preceding or following embodiment/feature/aspect, wherein the fermentation substrate comprises corn.

39. A fermentation nutrient composition comprising:
corn steep liquor;
at least one of (a) at least one surfactant, such as a nonionic surfactant, an amphoteric surfactant, or any combination thereof, or
(b) at least one antifoaming agent, or any combination thereof.

40. The fermentation nutrient composition of any preceding or following embodiment/feature/aspect, wherein the at least one antifoaming agent is at least one organic antifoaming agent.

41. The fermentation nutrient composition of any preceding or following embodiment/feature/aspect, wherein the at least one organic antifoaming agent is a polyglycol, a blend of polyglycol and silicone, a fatty acid ethoxylate, an ethoxylated fatty amine, or any combination thereof.

42. The fermentation nutrient composition of any preceding or following embodiment/feature/aspect, wherein the at least one surfactant is a nonionic surfactant that is an ethoxylated sorbitan ester, a glyceride ethoxylate, an ethoxylated castor oil, an alcohol ethoxylate, an alkylphenol ethoxylate, a phenol ethoxylate, an amide ethoxylate, a fatty acid ethoxylate, a fatty amine ethoxylate, a fatty amide ethoxylate, a fatty mono or di-ethanolamide, an alkyl glycoside, a polyethylene glycol (PEG), an acetylenic glycol, a polypropylene glycol (PPG), a poloxamer, an alkali metal arylsulfonate, an ethoxylated fatty amide, or any combination thereof.

43. The fermentation nutrient composition of any preceding or following embodiment/feature/aspect, wherein the at least one surfactant is a nonionic surfactant that is an ethoxylated sorbitan ester (polysorbate).

44. The fermentation nutrient composition of any preceding or following embodiment/feature/aspect, wherein the at least one surfactant is a nonionic surfactant that has an HLB value of from about 7 to about 25, and the at least one organic antifoaming agent is a surfactant that has an HLB value of from about 1 to about 5.

45. The fermentation nutrient composition of any preceding or following embodiment/feature/aspect, wherein the nutrient composition comprises from about 1.0% to about 99.9% by weight of the corn steep liquor, from about 0.1% to about 50% by weight of the at least one antifoaming agent, and from about 0.1% to about 50% by weight of the at least one surfactant, based on total solids weight of the composition.

46. A liquid mixture comprising:
corn steep liquor, yeast culture; sugars, and
at least one of (a) at least one surfactant, or
(b) at least one antifoaming agent, or any combination thereof.

47. The liquid mixture of any preceding or following embodiment/feature/aspect, wherein the at least one antifoaming agent is an organic antifoaming agent, and the at least one surfactant is a nonionic surfactant, an amphoteric surfactant, or any combination thereof.

48. The liquid mixture of any preceding or following embodiment/feature/aspect, wherein the at least one organic antifoaming agent is a surfactant that has an HLB value of from about 1 to about 5, and the at least one surfactant is a nonionic surfactant that has an HLB value of from about 7 to about 25.

The present invention can include any combination of these various features or embodiments above and/or below as set forth in sentences and/or paragraphs. Any combination of disclosed features herein is considered part of the present invention and no limitation is intended with respect to combinable features.

Applicants specifically incorporate the entire contents of all cited references in this disclosure. Further, when an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

It will be apparent to those skilled in the art that various modifications and variations can be made to the embodiments of the present invention without departing from the spirit or scope of the present invention. Thus, it is intended that the present invention covers other modifications and variations of this invention provided they come within the scope of the appended claims and their equivalents.

What is claimed is:
1. A method for enhancing yeast growth for bioproduct production, comprising:
    culturing at least one yeast in a growth medium containing a nutrient composition to obtain a propagated yeast culture, wherein the nutrient composition comprises corn steep liquor and at least one of (a) at least one antifoaming agent, or (b) at least one surfactant, or any combination thereof,
    wherein the at least one yeast is *Saccharomyces cerevisiae, Saccharomyces pastorianus (carlsbergiensis), Kluyveromyces lactis, Kluyveromyces fragilis, Fusarium oxysporum*, or any combination thereof,
    wherein the at least one organic antifoaming agent is a polyglycol, a blend of polyglycol and silicone, a fatty acid ethoxylate, an ethoxylated fatty amine, or any combination thereof, and
    wherein the at least one surfactant is a nonionic surfactant that is an ethoxylated sorbitan ester, a glyceride ethoxylate, an ethoxylated castor oil, an alcohol ethoxylate, an alkylphenol ethoxylate, a phenol ethoxylate, an amide ethoxylate, a fatty acid ethoxylate, a fatty amine ethoxylate, a fatty amide ethoxylate, a fatty mono or di-ethanolamide, an alkyl glycoside, a polyethylene glycol (PEG), an acetylenic glycol, a polypropylene glycol (PPG), a poloxamer, an alkali metal arylsulfonate, an ethoxylated fatty amide, or any combination thereof,
    and wherein a) addition of the nutrient composition results in an increased yeast concentration in the propagation and fermentation tanks of at least 3 million cells per gram as compared to a yeast concentration in the propagation and fermentation tanks wherein the culturing is done with addition of only the same amount of said corn steep liquor and without the at least one antifoaming agent, or
    wherein b) addition of the nutrient composition results in an increased ethanol concentration in the fermented biomass of at least 1% w/v as compared to an ethanol concentration in the propagation and fermentation tanks wherein the culturing is done with addition of only the same amount of corn steep liquor and without the at least one antifoaming agent and at least one surfactant, or both.
2. The method of claim 1, wherein the nutrient composition comprises the at least one surfactant.
3. The method of claim 1, wherein the at least one antifoaming agent is present.
4. The method of claim 3, wherein the at least one antifoaming agent is at least one surfactant that has an HLB value of from 1 to 5.
5. The method of claim 2, wherein the at least one surfactant is said ethoxylated sorbitan ester (polysorbate).
6. The method of claim 2, wherein the at least one surfactant has an HLB value of from 2 to 39.
7. The method of claim 2, wherein the at least one surfactant has an HLB value of from 7 to 25.
8. The method of claim 2, wherein the nutrient composition comprises from 95% to 99.9% by weight of the corn steep liquor, and at least one of (a) from 0.1% (w/v) to 5.0% (w/v) of the at least one antifoaming agent, or (b) from 0.1% (w/v) to 5.0% (w/v) of the at least one surfactant, or any combination of (a) and (b), based on total solids weight of the composition.
9. The method of claim 1, wherein the culturing comprises culturing a mixture containing from 0.01% to 50.00% by weight of the at least one yeast and from 99.99% to 50.00% by weight of the nutrient composition, based on the weight of the mixture.
10. The method of claim 1, wherein addition of the nutrient composition results in an increased yeast concentration in the propagated yeast culture of at least 25% more on a cells per unit weight basis as compared to a yeast concentration in the propagated yeast culture wherein the culturing is done with addition of only the same amount of said corn steep liquor and without the at least one antifoaming agent.
11. The method of claim 2, wherein addition of the nutrient composition results in an increased yeast concentration in the propagated yeast culture of at least 25% more on a cells per unit weight basis as compared to a yeast concentration in the propagated yeast culture wherein the culturing is done with addition of only the same amount of said corn steep liquor and without the at least one surfactant and the at least one antifoaming agent.
12. A method for fermentative bioproduct production, comprising: culturing at least one yeast in a growth medium containing a nutrient composition to obtain a propagated yeast culture, wherein the nutrient composition comprises corn steep liquor and at least one of (a) at least one antifoaming agent wherein the at least one organic antifoaming agent is a polyglycol, a blend of polyglycol and silicone, a fatty acid ethoxylate, an ethoxylated fatty amine, or any combination thereof, or (b) at least one surfactant wherein the at least one surfactant is a nonionic surfactant that is an ethoxylated sorbitan ester, a glyceride ethoxylate, an ethoxylated castor oil, an alcohol ethoxylate, an alkylphenol ethoxylate, a phenol ethoxylate, an amide ethoxylate, a fatty acid ethoxylate, a fatty amine ethoxylate, a fatty amide ethoxylate, a fatty mono or di-ethanolamide, an alkyl glycoside, a polyethylene glycol (PEG), an acetylenic glycol, a polypropylene glycol (PPG), a poloxamer, an alkali metal arylsulfonate, an ethoxylated fatty amide, or any combination thereof,
    wherein said at least one yeast comprises *Saccharomyces cerevisiae, Saccharomyces pastorianus (carlsbergiensis), Kluyveromyces lactis, Kluyveromyces fragilis, Fusarium oxysporum*, or any combinations thereof;
    inoculating a fermentation substrate with the propagated yeast culture to produce a fermentable biomass;
    fermenting the fermentable biomass to produce a fermented biomass comprising at least one bioproduct and non-fermented solids content; and
    separating at least a portion of the at least one bioproduct from the solids content,
    wherein a) addition of the nutrient composition results in an increased yeast concentration in the propagation and fermentation tanks of at least 3 million cells per gram as compared to a yeast concentration in the propagation and fermentation tanks wherein the culturing is done with addition of only the same amount of said corn steep liquor and without the at least one antifoaming agent, or
    wherein b) addition of the nutrient composition results in an increased ethanol concentration in the fermented biomass of at least 1% w/v as compared to an ethanol concentration in the propagation and fermentation tanks wherein the culturing is done with addition of only the same amount of corn steep liquor and without the at least one antifoaming agent and at least one surfactant, or both.

13. The method of claim 12, wherein the corn steep liquor, the at least one antifoaming agent, and the at least one surfactant are premixed prior to addition for the culturing.

14. The method of claim 12, wherein the corn steep liquor, the at least one antifoaming agent, and the at least one surfactant are individually added for the culturing.

15. The method of claim 12, wherein the at least one antifoaming agent is at least one organic antifoaming agent.

16. The method of claim 15, wherein the at least one antifoaming agent is a surfactant that has a hydrophilic-lipophilic balance (HLB) value of from about 1 to about 5.

17. The method of claim 12, further comprising introducing additional nutrient composition comprising corn steep liquor, at least one antifoaming agent, and at least one surfactant, which is contained in the fermentable biomass.

18. The method of claim 17, wherein the corn steep liquor, the at least one antifoaming agent, and optionally the at least one surfactant are premixed prior to addition to the fermentable biomass.

19. The method of claim 17, wherein the corn steep liquor, the at least one antifoaming agent, and optionally the at least one surfactant are individually added for the fermentable mass.

20. The method of claim 12, wherein the at least one bioproduct is ethanol, oil, or a combination thereof.

21. The method of claim 12, wherein the separating comprises a) distilling ethanol from the fermented biomass, b) extracting oil from the fermented biomass, or c) both a) and b).

22. The method of claim 12, wherein the fermenting is a high gravity fermentation at from 30% to 40% fermentable solids, and addition of the nutrient composition results in an increased ethanol yield of at least 2% w/v as compared to the ethanol yield wherein the culturing is done with the same amount of urea in place of the nutrient composition.

23. The method of claim 12, wherein the propagation and fermentation tanks comprises an ethanol concentration of 0.02% to 18% w/v, and addition of the nutrient composition results in an increased yeast concentration in the fermented biomass of at least 2.5% on a cells per unit weight basis as compared to a yeast concentration in the fermented biomass wherein the culturing is done with addition of only the same amount of said corn steep liquor and without the at least one surfactant and the at least one antifoaming agent.

24. The method of claim 12, wherein addition of the nutrient composition results in decreased residual sugar concentration in the fermented biomass of at least 3% w/v as compared to a residual sugar concentration in the propagation and fermentation tanks wherein the culturing is done with addition of only the same amount of said corn steep liquor and without the at least one antifoaming agent.

25. The method of claim 12, wherein culturing is performed in a fermentation mode selected from batch fermentation, fed-batch fermentation, or continuous fermentation.

26. The method of claim 12, wherein fermenting is performed in a fermentation mode selected from batch fermentation, fed-batch fermentation, or continuous fermentation.

27. The method of claim 12, wherein the fermentation substrate comprises corn, wheat, rye, barley, sorghum, wood, willow and switch grass, corn stover, corn cobs, straw bagasse, sugar cane, molasses, sugar beet, tapioca (cassava), potatoes, paper and pulp mills waste, algae, wood, seeds, grasses, or any combination thereof.

28. The method of claim 12 wherein the fermentation substrate comprises corn.

* * * * *